United States Patent [19]
Drysdale et al.

[11] Patent Number: 6,020,499
[45] Date of Patent: Feb. 1, 2000

[54] CYCLIC CARBONATES AND THEIR REACTIONS WITH AMINES

[75] Inventors: Neville E. Drysdale, Newark, Del.; Mike Fryd, Moorestown, N.J.; Sape Quashie, Southfield, Mich.

[73] Assignee: E. I. du Pont Nemours and Company, Wilmington, Del.

[21] Appl. No.: 09/092,156

[22] Filed: Jun. 5, 1998

Related U.S. Application Data

[60] Provisional application No. 60/049,321, Jun. 11, 1997.
[51] Int. Cl.$^7$ .................................................. C07D 321/00
[52] U.S. Cl. ............................................ 549/228; 528/341
[58] Field of Search ............................. 549/228; 528/341

[56] References Cited

PUBLICATIONS

K. D. Weilandt, et al., *Makromol. Chem. Phys.*, 197, 3851–3856, Nov. 1996.

*Primary Examiner*—Rachel Gorr

[57] ABSTRACT

Six-membered cyclic carbonates (2-oxo-1,3-dioxanes) in which keto or carbohydrocarbyloxy groups are bound to the 5 position of the ring are disclosed. They react surprising quickly with primary or secondary cyclic amines, and the novel product hydroxyurethanes are useful as reactive diluents.

5 Claims, No Drawings

CYCLIC CARBONATES AND THEIR REACTIONS WITH AMINES

This application claims the priority benefit of U.S. Provisional Application No. 60/049,321, filed Jun. 11, 1997.

FIELD OF THE INVENTION

Six-membered cyclic carbonates substituted with keto or carbohydrocarbyloxy groups in the 5 position are described. These cyclic carbonates are especially reactive with primary and cyclic secondary amines to form novel hydroxyurethanes which are useful as monomers and reactive diluents.

TECHNICAL BACKGROUND

Cyclic carbonates are known to react with amines, such as primary amines, to form hydroxyurethanes. However, these reactions tend to be relatively slow, so this reaction has not been employed much for commercial uses. If methods could be found to speed up such reactions, they would be more useful for commercial uses.

K. D. Weilandt, et al., Makromol. Chem. Phys., vol. 197, p. 3851–3856 (1996) report the preparation and polymerization (to a polycarbonate) of "2-methoxycarbonyl-2-methyltrimethylenecarbonate". No mention is made of reaction with amines.

SUMMARY OF THE INVENTION

This invention concerns a process for the production of hydroxyurethanes by the reaction of a cyclic carbonate with a primary or cyclic secondary amine, wherein the improvement comprises, using as the cyclic carbonate a compound of the formula

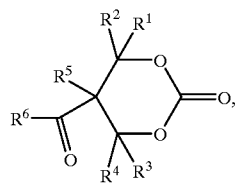

(I)

wherein:

$R^1$, $R^2$, $R^3$, $R^4$ and $R^5$ are each independently hydrogen, hydrocarbyl or substituted hydrocarbyl;

$R^6$ is hydrocarbyl, substituted hydrocarbyl or —$OR^7$; and $R^7$ is hydrocarbyl or substituted hydrocarbyl.

This invention also concerns a hydroxyurethane of the formula

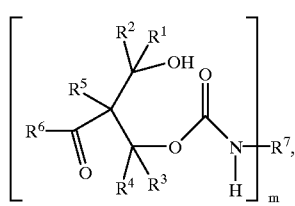

(II)

-continued

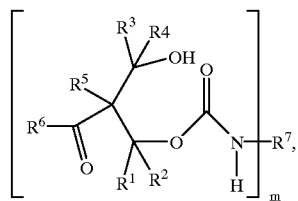

(III)

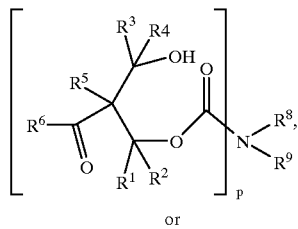

(IV)

or

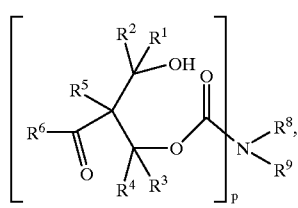

(V)

wherein:

$R^1$, $R^2$, $R^3$, $R^4$ and $R^5$ are each independently hydrogen, hydrocarbyl or substituted hydrocarbyl;

$R^6$ is hydrocarbyl, substituted hydrocarbyl or —$OR^{10}$;

$R^{10}$ is hydrocarbyl or substituted hydrocarbyl;

m is 1, 2, 3 or 4;

p is 1, 2 or 3;

$R^7$ is hydrocarbyl or substituted hydrocarbyl having m free valencies; and $R^8$ and $R^9$ taken together form a ring, said ring having p free valences to secondary nitrogen atoms.

Also described herein is a compound of the formula

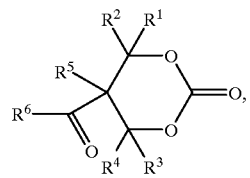

wherein:

$R^1$, $R^2$, $R^3$, $R^4$ and $R^5$ are each independently hydrogen, hydrocarbyl or substituted hydrocarbyl;

$R^6$ is hydrocarbyl, substituted hydrocarbyl or —$OR^{10}$; and $R^{10}$ is hydrocarbyl or substituted hydrocarbyl.

DETAILS OF THE INVENTION

The cyclic carbonates made and used herein are of the formula (I). Preferred cyclic carbonates have one or more of the following: $R^1$, $R^2$, $R^3$ and $R^4$ are hydrogen; and/or $R^5$ is alkyl containing 1 to 6 carbon atoms, more preferably methyl; and/or $R^6$ is alkyl containing 1 to 10 carbon atoms, more preferably methyl; and/or $R^6$ is —$OR^{10}$ wherein $R^{10}$ is hydrocarbyl, more preferably alkyl containing 1 to 10 carbon atoms, and especially preferably methyl.

In a another preferred form the group $R^{10}$, which may be substituted hydrocarbyl, may contain one or more of the grouping

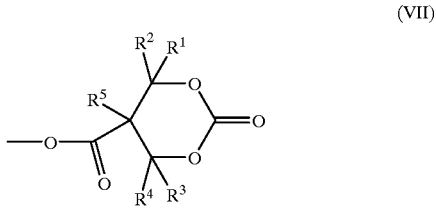

(VII)

wherein all of these groups (and all others in this paragraph) are as defined above. In other words, such compounds contain 2 or more cyclic carbonate groups of the type described for (I), and are included within the definition of (I). Such compounds are useful as crosslinking agents for polymers which contain groups that may react with cyclic carbonates, such as primary amines (see below). Compounds containing more than one such cyclic carbonate group may be made by the following route:

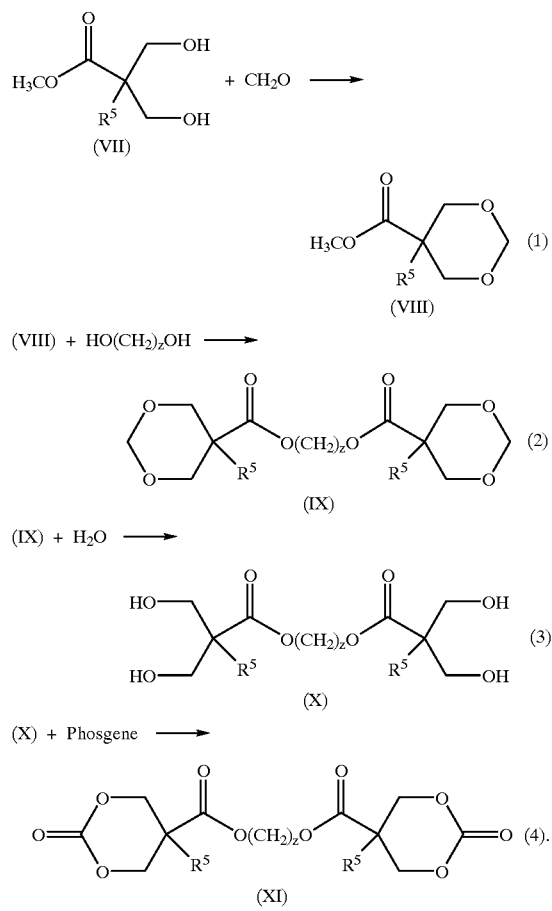

In Equations (1) and (3) a Bronsted acid is used as a catalyst, in Equation (2) a catalyst such as a tetraalkoxytitanate can be used, and in Equation 4 a phosgene source, such as triphosgene is preferred. Compounds such as (XI) containing more than 2 cyclic carbonate groups may be made simply by using an appropriate polyol in place of $HO(CH_2)_zOH$, wherein z is an integer of 2 or more. It is preferred that $R^{10}$ contain 1, 2 or 3 of the groups (VII), more preferably 1 such group.

Herein hydrocarbyl means a univalent radical containing only carbon and hydrogen. If not otherwise specified it is preferred that a hydrocarbyl or substituted hydrocarbyl radical contain 1 to about 30 carbon atoms. By substituted hydrocarbyl is meant a hydrocarbyl radical containing one or more substituents (functional groups) that do not interfere with the desired reaction(s) or with the stability of the compound involved. Suitable substituents herein include ether, oxo (keto), ester, halogen, amide and carbamate.

The 6-membered cyclic carbonates described herein may be made by methods illustrated in the Examples, see for instance Examples 1 and 2. Similar cyclic carbonates containing other groups and/or substituents may be made by analogous methods.

These carbonates may be reacted with a primary amine or a secondary cyclic amine. By a primary amine herein is meant the usual meaning, a compound containing the —$NH_2$ group. It is preferred that this group be bound to an alkyl-type carbon atom, i.e., $R^{11}R^{12}R^{13}CNH_2$ wherein $R^{11}$, $R^{12}$ and $R^{13}$ are each independently hydrogen, hydrocarbyl or substituted hydrocarbyl. In one preferred amine $R^{11}$, $R^{12}$ and $R^{13}$ are each independently hydrogen or alkyl, and more preferably $R^{11}$ and $R^{12}$ are hydrogen and $R^{13}$ is alkyl or cycloalkyl. The primary amine may contain more than one —$NH_2$ group. When this occurs, and the amine fully reacts, a compound such as (II) and/or (III) may be produced in which m is 2, 3 or 4. In one preferred reaction the primary amine contains 2, 3 or 4, more preferably 2 primary amine groups, so that in (II) and (III) produced m will be 2, 3 or 4, or 2 respectively. When m is more than 1, the starting primary amine would have the formula $R^7(NH_2)_m$, to give (II) and/or (III). Another preferred primary amine $H_2N(CH_2)_qNH_2$ wherein q is 2 to about 12.

The amine may also be a cyclic secondary amine of the type

(VI)

where the nitrogen is part of a ring. More than one secondary amine may be present in such a compound and the two amine nitrogen atoms need not be present in the same ring. The number of secondary cyclic amine groups present in the secondary cyclic amine corresponds to p in (IV) and (V) when the secondary cyclic amine is completely reacted. It is preferred that the secondary cyclic amine contain 2 or 3, more preferably 2, secondary cyclic amine groups. Thus it is also preferred in (IV) and (V) that p is 2 or 3, more preferably 2. Useful secondary cyclic amines include pyrrolidine, piperidene, and perhydropyrazine. Perhydropyrazine is a preferred secondary cyclic amine.

Amines containing both a primary amino group and a secondary cyclic amino group are also included within the definition of amines useful herein, and are considered primary amines and/or secondary cyclic amines.

It has surprisingly been found that the cyclic carbonates described herein react exceptionally rapidly with primary or secondary cyclic amines. This is an advantage in the preparation of hydroxyurethanes which can be made in less time and/or under milder conditions.

Temperature of the process is not critical, a preferred temperature range being about −20° C. to about 120° C., more preferably about 0° C. to about 60° C., and especially preferably about 10° C. to about 40° C. Ratios of reactants are not critical, but in order to most efficiently utilize the ingredients a molar ratio of about 1:1 for the cyclic carbonate and primary or secondary cyclic amine groups is preferred.

The reaction of cyclic carbonates with amines is a known reaction, see for instance British Patent 689,705, U.S. Pat. Nos. 3,072,613 and 4,882,391, and French Patent 1,096,204, all of which are hereby included by reference. In general all that is necessary for the reaction to occur is to bring the reactants into contact, as in solution, or if one or both of the amine and carbonate are liquids, without solvent for a period of time sufficient to carry out the reaction.

The hydroxyurethanes (II), (III), (IV) or (V), when m or p is 1 may be transesterified and polymerized to polyesters containing pendant urethane groups, which are useful for coatings. All of (II), (III), (IV) and (V) may be used in coating as reactive diluents, that is they may reduce the viscosity of a coating containing an already formed polymer, and then be incorporated into the coating solids by reaction of the hydroxyl group with another compound or polymer which contains groups that react with the hydroxyl group, such as isocyanate groups. If m or p in these hydroxyurethanes is more than 1, the hydroxyurethane may act as a crosslinking agent for a polymer (for example in a coating) which contain groups reactive with the hydroxyl group. The use of these hydroxyurethanes in coating is advantageous, since the presence of urethane groups in the final coating is advantageous, for example producing coatings with certain improved properties such as gloss, impact resistance, adhesion and toughness.

EXAMPLE 1

Preparation of 5-carbomethoxy-5-methyl-1,3-dioxan-2-one (2)

In a 500 mL three neck RB flask were added methyl 2,2-bis(hydroxymethyl)propionate (12.45 g) and tetrahydrofuran (THF) (100 mL). The resulting mixture was stirred under nitrogen via a mechanical stirrer until a homogeneous solution results. Triphosgene (8.78 g) was added and the solution cooled to −78° C. Triethylamine (18.3 g) was slowly added to the cooled solution. The resulting mixture was stirred at this temperature for one hour and then allowed to warm to room temperature. The triethylamine/HCl salt was filtered off and the resulting filtrate pass through a shallow bed of silica gel. The filtrate was concentrated at reduced pressure and then dried under vacuum affording 13.4 g of product which had a small amount of contamination. This contamination was removed via washing with warm diethyl ether. $^1$H NMR (CDCl$_3$) ppm: 4.67 (ab doublet, 2H), 4.20 (ab doublet, 2H), 3.77 (S, 3H), 1.30 (S, 3H).

EXAMPLE 2

Preparation of 5-Acetyl-5-methyl-1,3-dioxan-2-one (1)

In a one liter three neck flask equipped with a mechanical stirrer and under nitrogen were added triphosgene (37.0 g), 3,3-dihydroxymethyl-2-butanone (50 g) and THF (300 mL). The resulting mixture was stirred until a homogeneous solution resulted. This homogeneous solution was cooled to −78° C. Triethylamine (75.0 g) was added to the this solution over 30 min. The cold bath was removed and the reaction allowed to warm to room temperature. After stirring for one hour at room temperature the triethylamine/HCl salt was removed by filtration and the filtrate pass through a silica gel plug. The solvent was removed under reduced pressure resulting in an off white product. This product was then washed with hot ether giving a white solid. NMR analysis indicated that the product contained a small amount of triethylamine/HCl salt, thus the material was dissolved in dichloromethane and washed with water affording 15.02 g of material. $^1$H NMR (CDCl$_3$) ppm: 4.70 (ab doublet, 2H), 4.20 (ab doublet, 2H), 2.3 (S, 3H), 1.25 (S, 3H).

EXAMPLE 3

Reaction of 1 with N-Butylamine

In an oven dried 100 mL RB flask equipped with a stirrer and under nitrogen were added 1 (1.58 g, 0.01 mol), tetrahydrofuran (0.607 g) and tetrahydrofuran-d$_8$ (9.5 mL). After the formation of a homogeneous solution N-butylamine (0.73 g, 0.01 mol) was added and the solution was monitored via IR for the disappearance of the carbonate peak at ~1760 cm$^{-1}$. Upon completion the solvent was removed under vacuum resulting in 1.90 g of product $^1$H NMR (DMSO-d$_6$) ppm: 7.1 (t, 1H), 5.85 (t, 1H) 4.10 (ab q, 2H), 3.5 (m, 2H), 2.9 (q, 2H), 2.1 (s, 3H) 1.3 (m, 2H), 1.25 (m, 2H), 1.0 (s, 3H), 0.85 (t, 3H). $^{13}$C NMR (CDCl$_3$) ppm: 211.25, 156.63, 66.12, 64.26, 53.33, 40.65, 31.65, 25.78, 19.60, 16.76, 12.42. IR (THF) cm$^{-1}$: 1727 (s) and 1708 (m). MS: 232.1577 [M+H]$^+$ (100%). The product of the reaction was thus (II) in which R$^1$, R$^2$, R$^3$ and R$^4$ were hydrogen, R$^5$ was methyl, R$^6$ was methyl, R$^7$ was n-butyl and m was 1.

EXAMPLE 4

Reaction of 1 with 1,6-Hexamethylenediamine

In an oven dried 100 mL RB flask equipped with a stirrer and under nitrogen were added 1 (1.22 g, 0.0077 mol) and tetrahydrofuran (15.5 mL). After the formation of a homogeneous solution 1,6-hexamethylenediamine (0.463 g, 0.004 mol) was added. The solution was monitored via IR for the disappearance of the carbonate peak at ~1760 cm$^{-1}$. Upon completion the solvent was removed under vacuum resulting in 1.70 g of product. $^1$H NMR (DMSO-d$_6$) ppm: 7.1 (t, 2H), 5.85 (t, 2H) 4.10 (ab q, 4H), 3.5 (m, 4H), 2.9 (q, 4H), 2.1 (s, 6H) 1.35 (m, 4H), 1.2 (m, 4H), 1.0 (s, 6H). The product of the reaction was thus (II) in which R$^1$, R$^2$, R$^3$ and R$^4$ were hydrogen, R$^5$ was methyl, R$^6$ was methyl, R$^7$ was hexamethylene and m was 2.

EXAMPLE 5

Reaction of 2 with 1,6-Hexamethylenediamine

In an oven dried 100 mL RB flask equipped with a stirrer and under nitrogen were added 2 (1.74 g, 0.01 mol) and tetrahydrofuran (10.0 mL). After the formation of a homogeneous solution 1,6-hexamethylenediamine (0.58 g, 0.005 mol) was added. The solution was monitored via IR for the disappearance of the carbonate peak at ~1760 cm$^{-1}$. After completion, ~4 h, the resulting solution was concentrated at reduced pressure and then dried under vacuum affording 2.28 g of material. $^1$H NMR (DMSO-d$_6$) ppm: 7.10 (t, 2H), 4.90 (bs, 2H), 4.05 (ab q, 4H), 3.6 (s, 6H), 3.5 (s, 4H), 2.9 (q, 4H), 1.3 (m, 4H), 1.2 (m, 4H), 1.1 (s, 6H). IR (KBr) cm$^{-1}$: 1735 (s). MS (mass spectrum): 465.27 [M+H]$^+$ (100%). The product of the reaction was thus (II) in which $R^1$, $R^2$, $R^3$ and $R^4$ were hydrogen, $R^5$ was methyl, $R^6$ was methoxy, $R^7$ was hexamethylene and m was 2.

EXAMPLE 6

Reaction of 2 with 1,4-Diaminocyclohexane

In an oven dried 100 mL RB flask equipped with a stirrer and under nitrogen were added 2 (1.74 g, 0.01 mol) and tetrahydrofuran (10.0 mL). After the formation of a homogeneous solution 1,4-diaminocyclohexane (0.57 g, 0.005 mol) was added. The solution was monitored via IR for the disappearance of the carbonate peak at ~1760 cm$^{-1}$. After stirring overnight the reaction was concentrated at reduced pressure and then dried under vacuum affording 2.29 g of material. The product of the reaction was (II) in which $R^1$, $R^2$, $R^3$ and $R^4$ were hydrogen, $R^5$ was methyl, $R^6$ was methoxy, $R^7$ was 1,4-cyclohexylene and m was 2.

EXAMPLE 5

Reaction of 2 with Diethylenetriamine

In an oven dried 100 mL RB flask equipped with a stirrer and under nitrogen were added 2 (1.74 g, 0.01 mol) and tetrahydrofuran (10.0 mL). After the formation of a homogeneous solution diethylenetriamine (0.515 g, 0.0033 mol) was added. The solution was monitored via IR for the disappearance of the carbonate peak at ~1760 cm$^{-1}$. After ~3 h the reaction was concentrated at reduced pressure and then dried under vacuum affording 2.03 g of material. $^1$H NMR (DMSO-d$_6$) ppm: 7.05 (t, 2H), 4.95 (bs, 2H), 4.00 (ab q, 4H), 3.6 (s, 6H), 3.5 (s, 4H), 3.00 (q, 4H), 2.5 (m, 5H), 1.1 (s, 6H). The product of the reaction was thus (II) in which $R^1$, $R^2$, $R^3$ and $R^4$ were hydrogen, $R^5$ was methyl, $R^6$ was methoxy, $R^7$ was —CH$_2$CH$_2$NHCH$_2$CH$_2$—, and m was 2.

EXAMPLE 6

This Example illustrates the exceptionally rapid reaction between the cyclic carbonates described herein and amines.

The control reaction was the rate of reaction of the cyclic carbonate of trimethylolpropane (TMP carbonate, 5-hydroxymethyl-1,3-dioxan-2-one) with n-butylamine. In an oven dried 100 mL flask equipped with a stirrer and under nitrogen, THF (0.564 g., 7.88 mmol), THF-d$_8$ (9.5 mL) and TMP carbonate (1.601 g, 10.0 mmol). To this stirred solution n-butylamine (0.7314 g, 10 mmol) was added, a sample was immediately withdrawn and reaction monitored via $^1$H NMR, in which the carbonate concentration was calculated from the disappearance of the carbonate ab doublet with THF as the internal standard.

The reaction of 2 with n-butylamine was compared to the reaction of TMP carbonate with n-butylamine. In an oven dried 100 mL flask equipped with a stirrer and under nitrogen, THF (0.587 g, 8.20 mmol), THF-d$_8$ (9.5 mL) and 2 (1.74 g, 10.0 mmol). To this stirred solution n-butylamine (0.7314 g, 10 mmol) was added, a sample was immediately withdrawn and reaction monitored via $^1$H NMR, in which the carbonate concentration was calculated from the disappearance of the carbonate ab doublet with THF as the internal standard.

The results of both of these reactions are given in Table I.

TABLE I

| Time(min) | 2(mmol) Remaining | Time(min) | TMP Carbonate(mmol) Remaining |
|---|---|---|---|
| 0 | 10.0 | 0 | 10.0 |
| 10 | 1.092 | 17 | 4.70 |
| 25 | 1.083 | 47 | 2.66 |
| 40 | 0.619 | 74 | 1.88 |
| 55 | 0.404 | 107 | 1.41 |
| 85 | 0.304 | 134 | 0.94 |
|  |  | 164 | 0.78 |
|  |  | 194 | 0.31 |

It is evident that 2 reacts much more rapidly with n-butylamine than TMP carbonate.

What is claimed is:

1. A compound of the formula

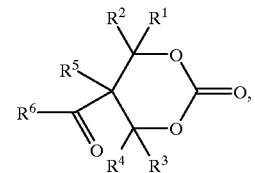

wherein:
 $R^1$, $R^2$, $R^3$, $R^4$ and $R^5$ are each independently hydrogen, hydrocarbyl or substituted hydrocarbyl;
 $R^6$ is hydrocarbyl, substituted hydrocarbyl or —OR$^{10}$; and
 $R^{10}$ is hydrocarbyl or substituted hydrocarbyl.

2. The compound as recited in claim 1 wherein:
 $R^1$, $R^2$, $R^3$ and $R^4$ are hydrogen;
 $R^5$ is alkyl containing 1 to 6 carbon atoms; and
 $R^6$ is alkyl containing 1 to 10 carbon atoms or $R^6$ is —OR$^{10}$ wherein R$^{10}$ is alkyl containing 1 to 10 carbon atoms.

3. The compound as recited in claim 2 wherein $R^6$ is methyl, or $R^6$ is —OR$^{10}$ wherein R$^{10}$ is methyl.

4. The compound as recited in claim 1 wherein $R^6$ is —OR$^{10}$, and R$^{10}$ contains 1, 2 or 3 of the grouping (VII)

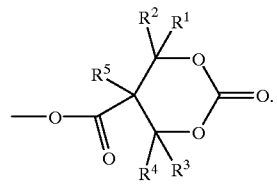

5. The compound as recited in claim 1 wherein $R^6$ is —OR$^{10}$, and R$^{10}$ contains one the grouping (VII)

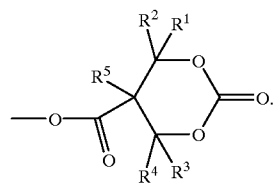

* * * * *